United States Patent [19]

Jehle

[11] Patent Number: 5,713,873
[45] Date of Patent: Feb. 3, 1998

[54] HYPODERMIC NEEDLE ASSEMBLY

[75] Inventor: Albert J. Jehle, Langhorne, Pa.

[73] Assignee: Marlene J. Mash, Yardley, Pa.

[21] Appl. No.: 138,359

[22] Filed: Oct. 18, 1993

[51] Int. Cl.$^6$ ..................................................... A61M 5/32
[52] U.S. Cl. ........................................ 604/198; 604/192
[58] Field of Search ............................... 604/192–198,
604/187, 263, 110, 218, 232; 128/919

[56] References Cited

U.S. PATENT DOCUMENTS

| | | | |
|---|---|---|---|
| 4,295,476 | 10/1981 | Quaas | 128/764 |
| 4,892,107 | 1/1990 | Haber | 128/763 |
| 4,946,447 | 8/1990 | Hardcastle et al. | 604/198 |
| 4,947,863 | 8/1990 | Haber et al. | 128/764 |
| 4,994,045 | 2/1991 | Ranford | 604/198 |
| 5,067,490 | 11/1991 | Haber | 128/763 |
| 5,104,385 | 4/1992 | Huband . | |
| 5,120,311 | 6/1992 | Sagstetter et al. . | |
| 5,137,521 | 8/1992 | Wilkins | 604/198 |
| 5,141,500 | 8/1992 | Hake | 604/198 |
| 5,188,601 | 2/1993 | King . | |
| 5,232,457 | 8/1993 | Grim | 604/195 |
| 5,242,416 | 9/1993 | Hutson . | |
| 5,242,419 | 9/1993 | Kiner et al. . | |
| 5,242,420 | 9/1993 | Martin . | |
| 5,254,100 | 10/1993 | Huband . | |
| 5,267,977 | 12/1993 | Feeney, Jr. | 604/198 |
| 5,279,579 | 1/1994 | D'Amico | 604/192 |

*Primary Examiner*—Michael Powell Buiz
*Assistant Examiner*—A. T. Nguyen
*Attorney, Agent, or Firm*—Howson and Howson

[57] ABSTRACT

In a hypodermic needle assembly, a needle is supported on a neoprene piston which is slidable in a tube. A syringe consisting of a barrel and a plunger is insertible into one end of the tube and connectible to, and disconnectible from, the needle by means of a Luer fitting. A projection on the plunger fits into a slot in the wall of the tube to prevent rotation of the plunger and limit its axial movement. In an alternative version, U-shaped slots in the wall of the tube provide tabs which can be manually compressed against the plunger to prevent its rotation as the syringe is connected to, and disconnected from, the needle. The assembly allows for injections from multiple syringes without removal of the needle from the patient. It also allows the needle to be withdrawn to a protected position within the tube and permits the protected needle and the syringe to be discarded separately.

12 Claims, 1 Drawing Sheet

HYPODERMIC NEEDLE ASSEMBLY

BRIEF SUMMARY OF THE INVENTION

This invention relates to hypodermic needle assemblies, and more particularly to improved hypodermic needle assemblies which reduce the chances of accidental needle sticks, which provide for safer disposal of used needles, and which provide for multiple injections through a single needle, without removal of the needle from the patient.

The increasing concern over blood-borne pathogens has precipitated numerous measures to prevent accidental needle sticks. Government regulations, and standards promulgated privately by health care facilities and organizations have called for various safety measures, including the use of special "sharps" containers for disposal of used needles, and prohibitions against bending used needles and against the replacement of caps on used needles. In addition, numerous devices have been developed, including special holders for needle caps so that the caps need not be held by the fingers, and special injection devices, such as the retractable needle device described in U.S. Pat. No. 5,188,601. In the device described in U.S. Pat. No. 5,188,601, a needle is frictionally held at the distal end of a barrel, and a plunger, slidable in the barrel, is connectible to the needle by a bayonet joint which allows the user, by pulling on the plunger, to withdraw the needle into the barrel after use.

In various branches of medicine, it is desirable to make multiple injections at the same site. For example, in the practice of dermatology, where a lesion is to be excised from a patient's skin, a local anaesthetic is administered by injection. The local anaesthetic is typically lidocaine, with a quantity of epinephrine to constrict the blood vessels and thereby prolong the effect of the anaesthetic. The administration of the anaesthetic causes a burning sensation, which can be avoided, or at least greatly diminished, by a preliminary injection of isotonic saline solution (0.9% by weight). The preliminary injection causes a swelling of the area surrounding the lesion, and prevents the burning sensation from being felt when the anaesthetic is subsequently administered.

The successive injections of saline solution and anaesthetic have been carried out in practice by injecting the saline with a first syringe having a needle, and thereafter withdrawing the first needle from the patient, and injecting the anaesthetic with a separate syringe having another needle. One problem in the case of successive injections is the need for insertion of two separate needles, or the removal and reinsertion of the same needle. Ordinarily the administration of successive injections is carried out by using two separate needles, each attached to its own syringe. In the past, it has not been practical to attempt to make a first injection, and thereafter detach the syringe from the needle while the needle is still in place, and replace it with a separate syringe. There was no easy way to attach the syringe to the needle while the needle remained inserted in the patient. Another problem was that the two separate syringes were subject to the same hazards as other conventional needles.

The principal object of this invention is to provide an improved hypodermic needle assembly which significantly reduces the risk of accidental injuries to the physician or nurse administering an injection. Another object of the invention is to provide for safe disposal of a hypodermic needle. Still another object of the invention is to provide for separate disposal of the needle and other essential parts of the syringe in order to discourage reuse of the needle by drug abusers. Still another object of the invention is to provide a simple and effective hypodermic needle assembly which facilitates the administration of successive injections through a single needle without removing the needle from the patient, thereby simplifying the administration of multiple, different substances by injection, and making it possible to administer large doses of a substance through a single needle without removing the needle from the patient.

A preferred hypodermic needle assembly in accordance with the invention comprises a tube having a wall with a cylindrical inner surface having a central axis, and having first and second openings at opposite ends. A piston having first and second opposite faces, has a hollow needle extending from the first face, and a fitting on the second face for disconnectible, fluid-tight attachment to a syringe. A passage within the piston provides fluid communication between the needle and the fitting. The piston is located within the tube and frictionally engages the cylindrical inner surface of the wall of the tube. However, the piston is axially slidable in the tube when subjected to an external force. The piston is engaged with the cylindrical inner surface at least at two axially spaced locations so that the needle is held substantially parallel to the central axis of the tube as the piston slides along the axis. The needle and piston are locatable entirely within the tube, and are axially movable to a position in which the needle extends outward from the first opening of the tube while the piston is inside the tube. A syringe is insertible into the second opening of the tube and has a tip detachably connectible to the fitting, and a plunger for forcing liquid through the tip and through the fitting, the passage and the needle. The barrel of the syringe is sufficiently long that the barrel extends outward from the second opening of the tube while the needle extends outward from the first opening.

Following the administration of an injection from the syringe through the needle, with the needle extending outward from the first opening of the tube, the needle can be withdrawn to a safe position within the tube by manually pulling on the barrel of the syringe, and the syringe can be thereafter detached from the fitting for separate disposal of the needle and syringe. With the needle extending outward from the first opening of the tube and into a patient, a substance can be injected into the patient through the needle from a first syringe attached to the fitting on the piston, and, without removing the needle from the patient, the first syringe can be disconnected from the fitting, a second syringe can be connected to the fitting, and a substance can be injected into the patient through the needle from the second syringe, and the needle can thereafter be withdrawn to a safe position in the tube by manually pulling on the barrel of the second syringe. The tube can be grasped manually to enable the syringe to be detached from the needle and replaced by another syringe without excessive movement of the needle.

Further objects, advantages and details of the invention will become apparent from the following detailed description, when read in conjunction with the drawings.

DETAILED DESCRIPTION

Figure 1:
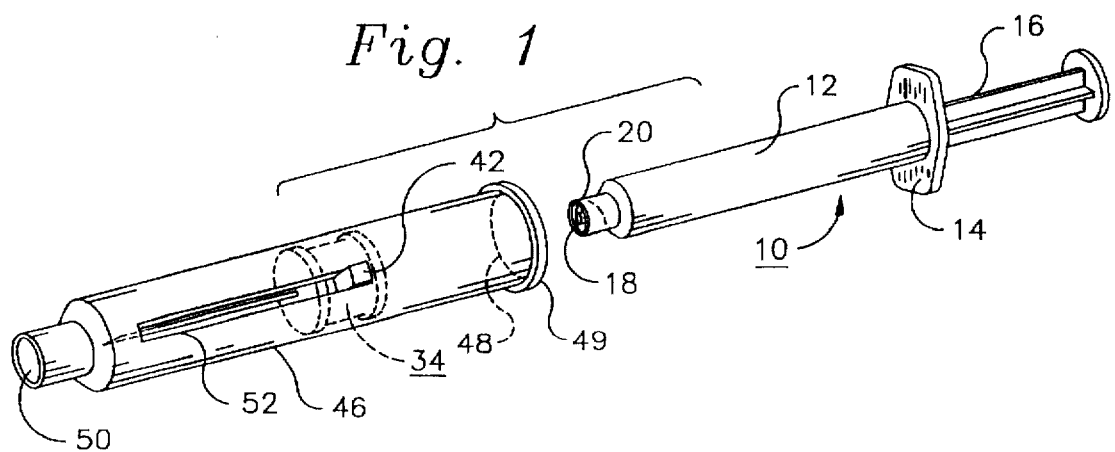
FIG. 1 is an exploded perspective view of a hypodermic needle assembly in accordance with a first embodiment of the invention, showing the needle in its withdrawn position, and also showing a syringe.

In the exploded view of FIG. 1, reference numeral 10 denotes a conventional disposable syringe comprising a barrel 12 having a flange 14 integrally molded at its proximal end for engagement by the first and second fingers of the hand. The syringe also includes a thumb-operate plunger 16, which, when depressed, causes fluid to be ejected through a nozzle 18 at the distal end of the barrel. Surrounding the nozzle is a cylinder 20 which is internally threaded for engagement with a so-called "Luer" fitting provided on the distal end of a needle.

Figure 3:
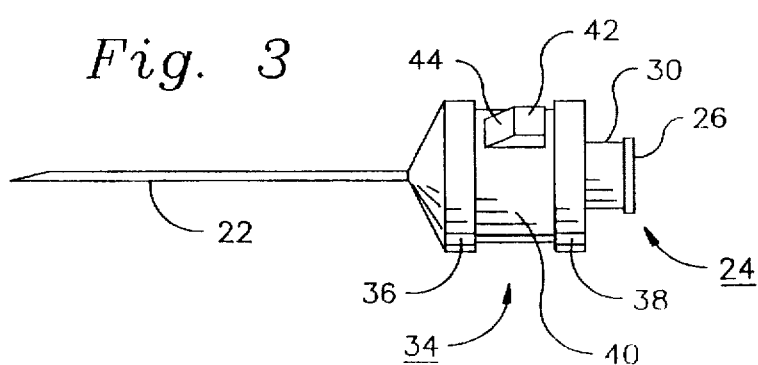
FIG. 3 is a side elevation of the needle, piston and fitting for disconnectible attachment to a syringe.
Figure 4:
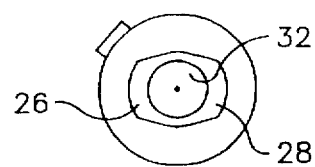
FIG. 4 is an end elevation of the needle, piston and fitting, as seen from the right side of FIG. 3.

A needle 22, shown in FIG. 3, is provided with a Luer fitting 24. This fitting, as shown in FIG. 4, comprises a pair of flanges 26 and 28 for engaging the internal threads of cylinder 20. These flanges are formed on the exterior of a cylindrical element 30 having a hollow passage 32 for receiving the nozzle 18 of the syringe and conducting fluid from the syringe into the needle. The Luer fitting provides for fluid-tight engagement of the needle with the syringe upon engagement of flanges 26 and 28 with the internal threads of cylinder 20 and clockwise rotation through approximately a quarter turn.

As shown in FIGS. 3 and 4, the needle is provided with a piston 34, located near the proximal end of the needle, but forward of the Luer fitting 24. This piston is preferably formed from neoprene. Piston 34 is preferably formed with radially coextensive forward and rear annular ridges 36 and 38. A reduced portion 40, between these ridges, has a projection 42 which extends radially slightly beyond the ridges. The projection has an oblique forward face, forming a ramp 44.

The assembly of FIG. 1 also includes a tube 46, preferably of polyethylene, and having a cylindrical inner surface, the diameter of which is slightly smaller than the relaxed diameter of ridges 36 and 38 of the piston. The tube has a rear opening 48, which allows the piston 34 to be introduced into the tube. The diameter of opening 48, which is the same as that of the cylindrical inner surface of tube 46, is larger than the outer diameter of the barrel 12 of syringe 10, and should be larger than the outer diameter of the largest syringe with which the tube 46 will be used. The rear opening is surrounded by a lip 49, which facilitates grasping of tube 46.

Figure 2:
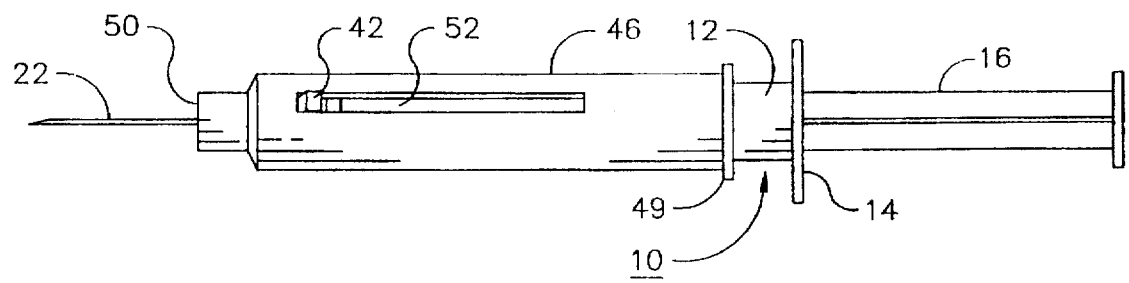
FIG. 2 is a side elevation of the hypodermic needle assembly of FIG. 1, showing the needle in its extended position.

Tube 46 has a reduced opening 50 at its distal end. This opening is located on the axis of the tube and allows the needle 22 to project forward from the tube as shown in FIG. 2. The reduced opening 50 is sufficiently small to prevent manual access to the tip of the needle 22 when the needle is completely withdrawn so that it is located entirely within the tube 46.

An axial slot 52 is formed in the wall of tube 46. Projection 42 is located in this slot, as shown in FIGS. 1 and 2. The engagement of the projection with the slot prevents rotation of the piston as the syringe is engaged with and disengaged from the needle. The slot also limits rearward axial movement of the needle. Thus, engagement of projection 42 with the proximal end of slot 52, as shown in FIG. 1, prevents the needle from being withdrawn from tube 46 through opening 48. The slot is preferably long enough to permit the piston to engage the forward end of the interior of tube 46 when the needle is in its fully projected condition, as shown in FIG. 2.

Because the neoprene piston, and its projection 42 are resilient, it is possible for the projection to be compressed radially inwardly so that the piston can be inserted into tube 46 through opening 48. The ramp 44 on projection 42 facilitates insertion of the piston into the tube. When projection 42 reaches slot 52, it snaps into the slot and remains engaged with the slot. The reduced portion 40 of the piston between ridges 36 and 38 allows room for deformation of projection 42 as the plunger is introduced into the tube during initial assembly.

When used to administer a single injection, the assembly of FIG. 1 can be initially in the condition shown, with the syringe 10 empty, the barrel of the syringe is inserted into opening 48 of the tube, and connected to the Luer fitting 24 (FIG. 4) by clockwise rotation of the barrel of the syringe about its axis. The syringe is then pushed forward into the tube to cause the needle 22 to project from the opening 50 at the distal end of the tube. At this time, the assembly will be in the condition depicted in FIG. 2. The needle can then be inserted through the rubber seal in a conventional vial containing the liquid to be administered by injection. Plunger 16 may be pushed forward to introduce air into the vial in order to pressurize the interior of the vial. Then, with the tip of the needle submerged in the liquid in the vial, the plunger is withdrawn to draw liquid into the syringe. The needle can then be inserted into the patient, with the assembly in the condition shown in FIG. 2. The liquid is injected by depression of plunger 16. After completion of the injection, the needle can be withdrawn from the patient, and pulled into the interior of the tube 46 by pulling flange 14 rearwardly relative to tube 46 until projection 42 contacts the proximal end of slot 52. The needle will now be held in a safe position within the tube, by the friction of the piston 34 against the interior wall of the tube. With the needle safely in the tube, the syringe can be rotated counterclockwise relative to the tube to disconnect the syringe from the Luer fitting on the needle. Then, the syringe 10 can be discarded separately from the tube containing the needle. Since the needle is useless without the syringe, and the syringe is useless without the needle, separate disposal affords a measure of protection against misuse of the needle and syringe.

When the device is to be used to administer multiple injections through the same needle without withdrawing the needle from the patient, several syringes will normally be preloaded with the liquid or liquids to be injected. Preloading of multiple syringes is accomplished by inserting a needle into a vial through its rubber seal while the needle is attached to a first syringe, withdrawing a dose of the liquid into the syringe, and then detaching the syringe from the needle and successively attaching additional syringes to the needle to withdraw further doses from the vial. The use of the tube 46 to hold the needle makes it possible to control the position of the needle manually, and prevent its rotation, so that it can remain inserted through the rubber seal on the vial while several syringes are loaded through it. By enabling the user to control the position of the needle manually and to prevent rotation of the needle, the tube 46 makes it easy for the user to load multiple syringes.

In a similar manner, it is possible to load multiple syringes with different substances for successive injections of different substances through a single needle. Thus, a physician can have a supply of syringes preloaded with the appropriate substances before meeting with his or her patients.

When administering successive doses of the same or different substances through the same needle without withdrawing it from the patient, the physician will first need to obtain a loaded syringe, tube and needle assembly as shown in FIG. 2. This may be accomplished by inserting the needle of the syringe, tube and needle assembly into a vial and withdrawing liquid into the syringe. Alternatively, it may be accomplished by using a preloaded syringe. In the latter case, the preloaded syringe is attached to the Luer fitting on the needle by relative rotation, and residual air is removed from the needle by depressing plunger 16 slightly before inserting the needle into the patient. After the first dose is injected, the syringe is rotated counterclockwise and removed from the Luer fitting of the needle, while the tube is held manually to prevent it from rotating and from moving excessively. The needle remains in the patient. Then, a second syringe, preloaded with the same substance, or with a different substance, depending on what is required by the patient, is inserted into the tube and attached to the Luer fitting. The second dose is then injected by depression of the plunger of the second syringe. Still further doses can be administered in a similar manner from additional preloaded syringes. When the injections are completed, the needle is withdrawn from the patient, and pulled into the interior of the tube by pulling the syringe rearwardly while it is still attached to the needle. Then, the syringe is detached from the needle, and the syringe and the tube containing the needle are separately discarded.

The hypodermic needle assembly described above has, as its principal advantages, the fact that it allows for injections from multiple syringes without removal of the needle from the patient; the fact that it provides for control of the position of the needle in the patient, while one syringe is being replaced by another; and the fact that it allows the needle to be withdrawn to a protected position within the tube and permits the protected needle and the syringe to be discarded separately.

Figure 5:
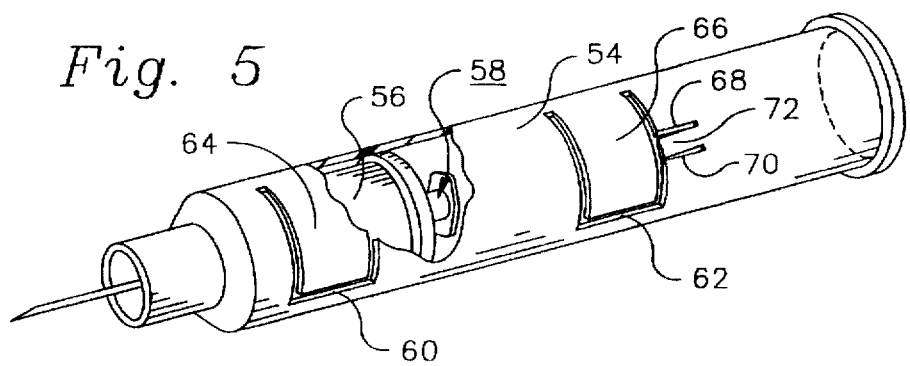
FIG. 5 is a perspective view of a hypodermic needle assembly in accordance with a second embodiment of the invention, partially cut away to show the piston.

Various modifications can be made to the device described above. Fore example, in the alternative version of the device as shown in FIG. 5, a tube 54, corresponding to tube 46, receives a piston 56 having a Luer fitting 58. The wall of the tube is provided with two U-shaped slots 60 and 62, to form flexible tabs 64 and 66, which can be manually pressed inward to engage the piston in order to prevent it from rotating as the syringe is engaged with, and disengaged from Luer fitting 58. Tab 64 is located near the distal end of tube 54 so that it can be engaged with piston 56 when the needle is in the fully projecting position. Tab 66 is located at a position such that it can be engaged with the piston when the needle is fully withdrawn into the interior of tube 54. Slots 68 and 70, which extend axially from the rearmost leg of U-shaped slot 62 form a tab 72. Tab 72 is bent slightly inward so that it provides a stop to engage piston 56 and prevent its withdrawal from tube 54.

Because the tube in FIG. 5 has inwardly bendable tabs for preventing rotation of piston 56 when the syringe is engaged with, and disengaged from, the needle, and a tab 72 for preventing withdrawal of the piston, it is not necessary for piston 56 to have a projection corresponding to projection 42 in FIG. 3.

Still other modifications to the device described above will occur to persons skilled in the art and can be made without departing from the scope of the invention as defined in the following claims.

I claim:

1. A hypodermic needle assembly comprising:

means providing a tube having a wall with a cylindrical inner surface having a central axis, and having first and second openings at opposite ends thereof;

a piston having first and second opposite faces, with a hollow needle extending from the first face, a fitting on the second face for disconnectible, fluid-tight attachment to a syringe, and means providing a passage within the piston for fluid communication between the needle and the fitting, the piston being located within the tube and frictionally engaging the cylindrical inner surface of the wall of the tube but being axially slidable therein when subjected to an external force, the piston being engaged with the cylindrical inner surface at least at two axially spaced locations whereby the needle is held substantially parallel to the central axis of the cylindrical inner surface of the wall of the tube as the piston slides along the axis, the needle and piston being locatable entirely within the tube, and axially movable to a position in which the needle extends outward from the first opening of the tube while the piston is inside the tube; and holding means for preventing rotation of the piston relative to the tube, the holding means comprising a flexible portion of the wall of the tube, the flexible portion being compressible inwardly against the piston by manual pressure exerted on the exterior of the tube while the inner surface of the other portions of the wall remains cylindrical, such that with the needle extending outward from the first opening of the tube and into a patient, a substance can be injected into the patient through the needle from a first syringe attached to the fitting on the piston, and, without removing the needle from the patient, the holding means can be used to prevent the piston from rotating relative to the tube so that the first syringe can be disconnected from the fitting, a second syringe can be connected to the fitting, and a substance can be injected into the patient through the needle from the second syringe, and the needle can thereafter be withdrawn to a safe position in the tube by manually pulling on the barrel of the second syringe.

2. A hypodermic needle assembly according to claim 1 in which the wall of the tube has a second portion which is compressible inwardly against the piston while the piston is located at a position in which the needle is located entirely within the tube.

3. A hypodermic needle assembly according to claim 1 in which the holding means for preventing relative rotation comprises at least one tab formed in the wall of the tube, the tab being compressible inwardly against the piston by manual pressure exerted on the tab.

4. A hypodermic needle assembly according to claim 3 including a second tab, also formed in the wall of the tube, and being compressible inwardly against the piston while the piston is located at a position in which the needle is located entirely within the tube.

5. A hypodermic needle assembly according to claim 1 including stop means on the cylindrical inner surface of the wall of the tube for engaging the piston when the needle and piston are located entirely within the tube, to prevent movement of the piston out of the tube through the second opening thereof.

6. A hypodermic needle assembly according to claim 1 in which the first opening of the tube is smaller than the transverse cross-section of the cylindrical inner wall of the tube.

7. A hypodermic needle assembly according to claim 1 in which the first opening of the tube is sufficiently small to prevent manual access to the tip of the needle when the needle and piston are located entirely within the tube.

8. A hypodermic needle assembly according to claim 1 in which said flexible portion of the wall is defined by slots formed in, and extending through, the wall.

9. A hypodermic needle assembly comprising:

means providing a tube having a wall with a cylindrical inner surface having a central axis, and having first and second openings at opposite ends thereof; and a piston having first and second opposite faces, with a hollow needle extending from the first face, a fitting on the second face for disconnectible, fluid-tight attachment to a syringe, and means providing a passage within the piston for fluid communication between the needle and the fitting, the piston being located within the tube and frictionally engaging the cylindrical inner surface of the wall of the tube but being axially slidable therein when subjected to an external force, the piston being engaged with the cylindrical inner surface at least at two axially spaced locations whereby the needle is held substantially parallel to the central axis of the cylindrical inner surface of the wall of the tube as the piston slides along the axis, the needle and piston being locatable entirely within the tube, and axially movable to a position in which the needle extends outward from the first opening of the tube while the piston is inside the tube;

wherein the wall of the tube has portions which are compressible inwardly against the piston by manual pressure exerted on the exterior of the tube while the inner surface of the other portions of the wall remains cylindrical, to prevent the piston from rotating relative to the tube both when the piston is located so that the needle extends outwardly from the first opening and when the piston is located so that the needle is located entirely within the tube.

10. A hypodermic needle assembly according to claim 9 in which said flexible portions of the wall are defined by slots formed in, and extending through, the wall.

11. A hypodermic needle assembly comprising:

means providing a tube having a wall with a cylindrical inner surface having a central axis, and having first and second openings at opposite ends thereof;

a piston having first and second opposite faces, with a hollow needle extending from the first face, a fitting on the second face for disconnectible, fluid-tight attachment to a syringe, and means providing a passage within the piston for fluid communication between the needle and the fitting, the piston being located within the tube and frictionally engaging the cylindrical inner surface of the wall of the tube but being axially slidable therein when subjected to an external force, the piston being engaged with the cylindrical inner surface at least at two axially spaced locations whereby the needle is held substantially parallel to the central axis of the cylindrical inner surface of the wall of the tube as the piston slides along the axis, the needle and piston being locatable entirely within the tube, and axially movable to a position in which the needle extends outward from the first opening of the tube while the piston is inside the tube; and holding means for preventing rotation of the piston relative to the tube, the holding means comprising a flexible portion of the wall of the tube, the flexible portion being compressible inwardly against the piston by manual pressure exerted on the exterior of the tube while the inner surface of the other portions of the wall remains cylindrical, the flexible means being positioned to prevent the piston from rotating relative to the tube when the needle is located entirely within the tube.

12. A hypodermic needle assembly according to claim 11 in which said flexible portion of the wall is defined by slots formed in, and extending through, the wall.

* * * * *

UNITED STATES PATENT AND TRADEMARK OFFICE
CERTIFICATE OF CORRECTION

PATENT NO. : 5,713,873
DATED : February 3, 1998
INVENTOR(S) : Albert J. Jehle

It is certified that error appears in the above-indentified patent and that said Letters Patent is hereby corrected as shown below:

Column 3, line 18, replace "distal" with "proximal";

Column 5, line 39, replace "Fore" with "For";

Column 7, line 33, replace "flexible" with "compressible";

Column 8, line 29, replace "means" with "portion".

Signed and Sealed this

Seventh Day of July, 1998

Attest:

BRUCE LEHMAN

*Attesting Officer*   *Commissioner of Patents and Trademarks*